US00PP37169P3

(12) United States Plant Patent
Pitts

(10) Patent No.: US PP37,169 P3
(45) Date of Patent: Dec. 23, 2025

(54) APPLE TREE NAMED 'MAIA-MITCHELL'

(50) Latin Name: ***Malus* x *domestica***
Varietal Denomination: MAIA-MITCHELL

(71) Applicant: Midwest Apple Improvement Association, Oberlin, OH (US)

(72) Inventor: William A Pitts, Sterling, NY (US)

(73) Assignee: Midwest Apple Improvement Association, Amherst, OH (US)

( * ) Notice: Subject to any disclaimer, the term of this patent is extended or adjusted under 35 U.S.C. 154(b) by 165 days.

(21) Appl. No.: 18/130,019

(22) Filed: Apr. 3, 2023

(65) Prior Publication Data

US 2024/0334851 P1 Oct. 3, 2024

(51) Int. Cl.
*A01H 5/08* (2018.01)
*A01H 6/74* (2018.01)

(52) U.S. Cl.
USPC ..... Plt./161
CPC ..... *A01H 6/7418* (2018.05); *A01H 5/08* (2013.01)

(58) Field of Classification Search
USPC ..... Plt./161
CPC ..... A01H 5/08; A01H 5/00; A01H 6/7418; A01H 6/74
See application file for complete search history.

(56) References Cited

U.S. PATENT DOCUMENTS

PP11,226 P * 2/2000 Turner ..... Plt./161

* cited by examiner

*Primary Examiner* — June Hwu
(74) *Attorney, Agent, or Firm* — Weatherly IP Solutions, LLC; Karen P. Bechtold; James Weatherly

(57) ABSTRACT

A new and distinct variety of apple tree named 'MAIA-MITCHELL' that ripens in late October with strong, solid red coloration and that maintains firmness and quality for 6 months under commercial refrigeration conditions, is disclosed herein.

5 Drawing Sheets

Latin name of the genus and species of the plant claimed: *Malus* x *domestica.*

Variety denomination: 'MAIA-MITCHELL'.

BACKGROUND OF THE INVENTION

A new and distinct variety of apple was identified as a limb mutation of the *Malus domestica* variety 'MAIA1' (U.S. Plant Pat No. 24,579). The limb mutation was initially identified in 2018 among trees growing on a commercial apple orchard in Wolcott, New York, located in Wayne County. The 'MAIA1' tree containing the mutation was planted in a commercial block on Budagovsky-9 (Bud-9 or B9, unpatented) rootstock in 2014. The novel variety described herein is identifiably distinct from the parent variety by the earlier, much brighter, and more complete red coloring of the fruit. Budwood from the original tree was collected and the new variety of apple tree was asexually reproduced by grafting on a Standard rootstock in Sterling, New York, located in Cayuga County. The first generation was grafted in 2019. Asexual propagation shows the unique combination of characteristics and distinct color are true to the description contained herein through successive generations. A third generation was budded in 2021 on three commercial rootstocks (Budagovsky-9, G.11 and G.935), also in Sterling New York. While chip-budding was used initially to reproduce the new apple tree variety, it is expected that other industry recognized grafting methods would be effective.

'Fuji' is the most closely related commercial variety to the new apple variety described herein. 'MAIA-MITCHELL' is distinguished from 'Fuji' in that it matures one week before 'Fuji', its fruit skin has a more complete strong red coloring as opposed to the bicolored moderate red coloring of 'Fuji', and the fruit has a roundish oblate shape as opposed to the 'Fuji' apple's oval, slightly flattened shape.

The new variety, named 'MAIA-MITCHELL' is distinct from 'MAIA1' as 'MAIA-MITCHELL' possesses a much higher percentage of red coloration (up to 90%), a darker coloration (Strong-red 46A as opposed to Orange-Red N34A of the parent variety), and shows significant fruit color up to eight weeks earlier than the parent variety. The fruit of 'MAIA-MITCHELL' are medium sized, extremely crisp, sweet, and with long storability. The development of early, significant coloration of apple fruits is a desirable commercial attribute, as it allows growers to harvest at optimum maturity without waiting for commercially desirable color to develop.

BRIEF DESCRIPTION OF THE DRAWINGS

The accompanying photographs show typical specimens of the new variety as depicted in color as nearly true as is reasonably possible. 'MAIA-MITCHELL' photographs were taken in Wayne and Cayuga Counties, New York.

DETAILED BOTANICAL DESCRIPTION

Figure 1:
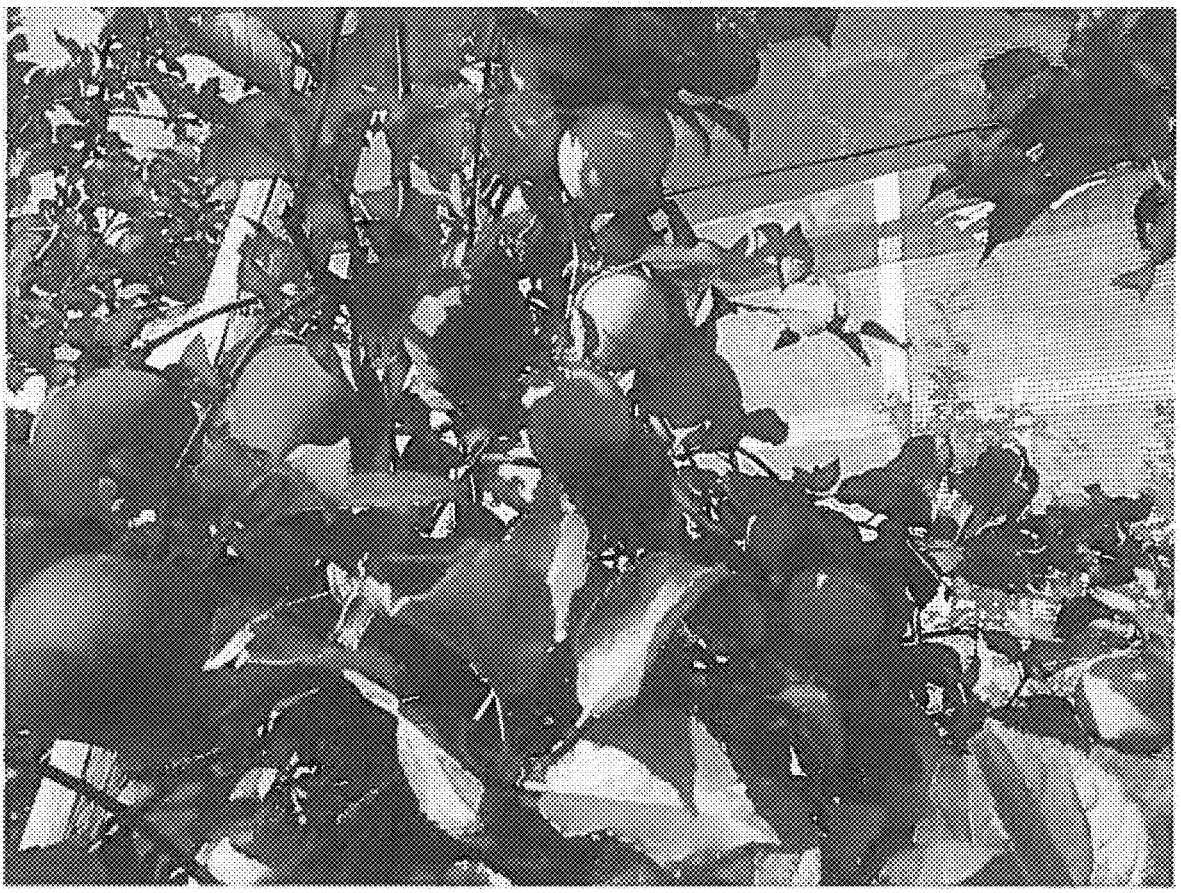
FIG. 1. Shows the original 'MAIA-MITCHELL' limb mutation (in foreground) on the parent 'MAIA1' tree, in Wolcott, New York. The photograph was taken Sep. 28, 2019 when the tree was five years old.
Figure 2:
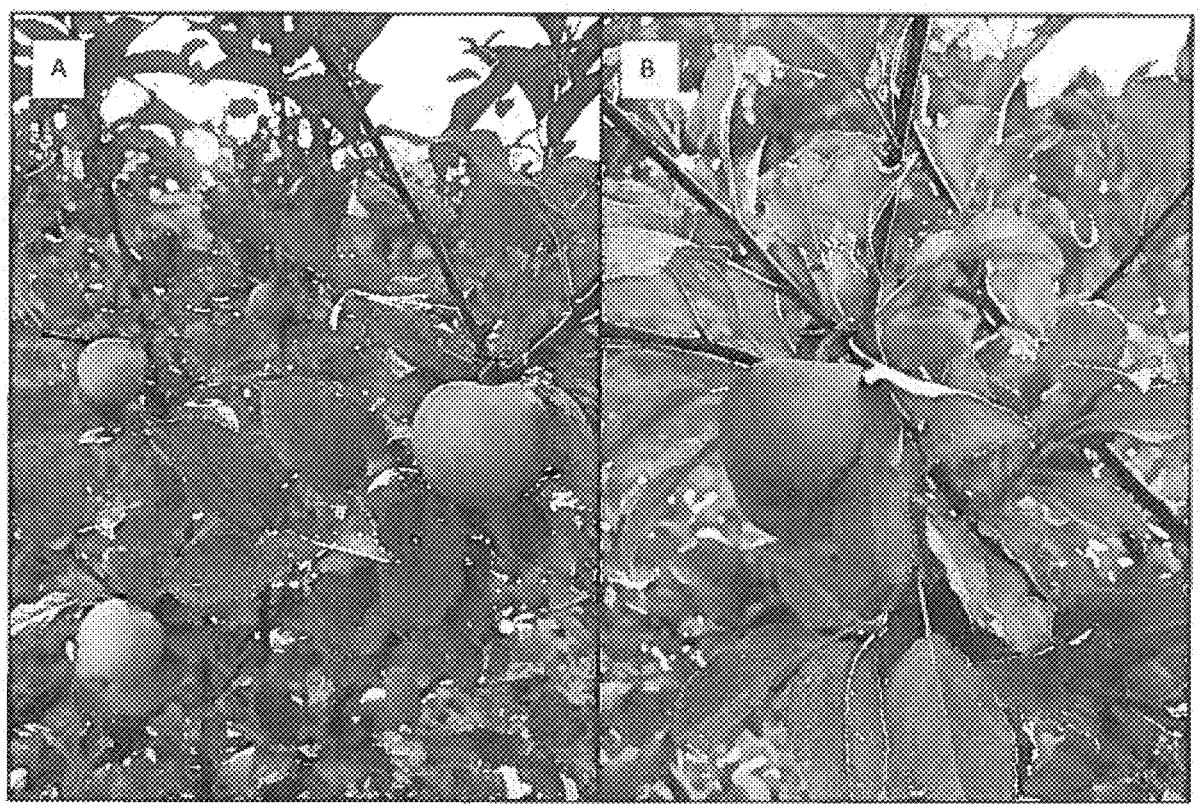
FIG. 2. Shows the difference in coloration between 'MAIA1' (Panel A) and 'MAIA-MITCHELL' (Panel B) on Aug. 15, 2022, roughly ten weeks prior to harvest. Both trees were grafted by chip-budding onto seedling rootstocks in 2020 in Sterling, New York.
Figure 3:
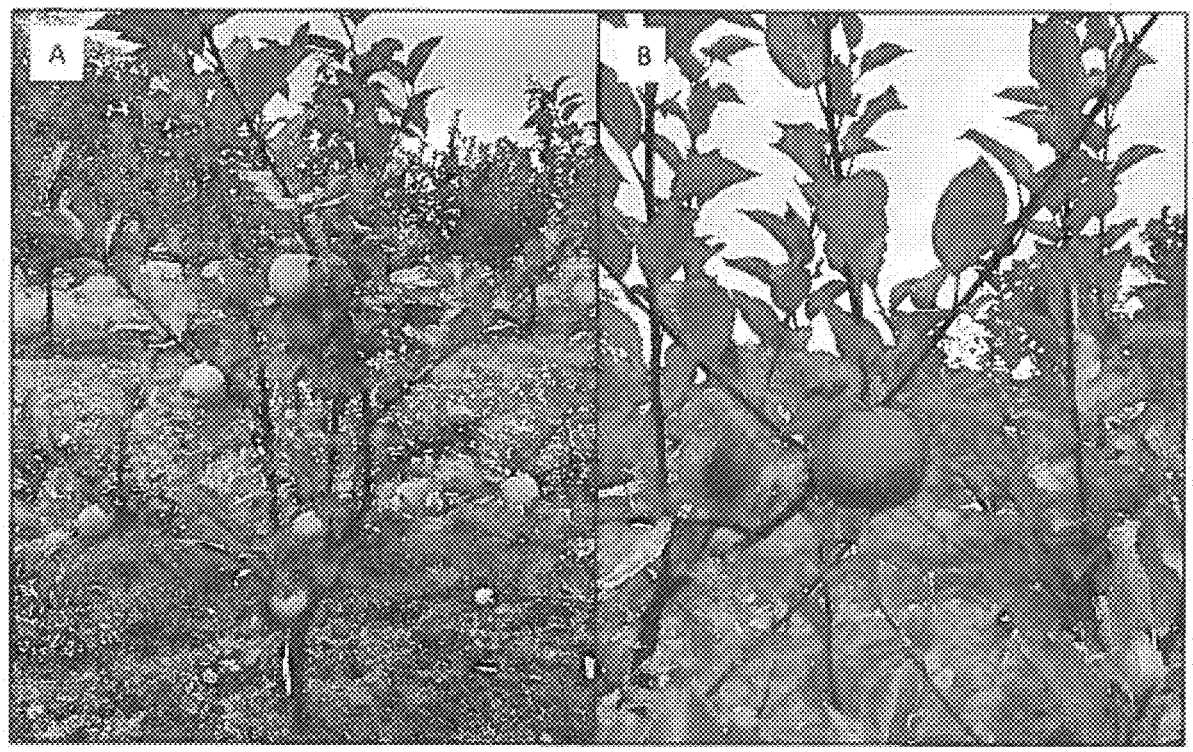
FIG. 3. Shows the difference in coloration between 'MAIA1' (Panel A) and 'MAIA-MITCHELL' (Panel B) on Sep. 8, 2022, roughly seven weeks prior to harvest. Both trees were grafted by chip-budding onto seedling rootstocks in 2020 in Sterling, New York.
Figure 4:
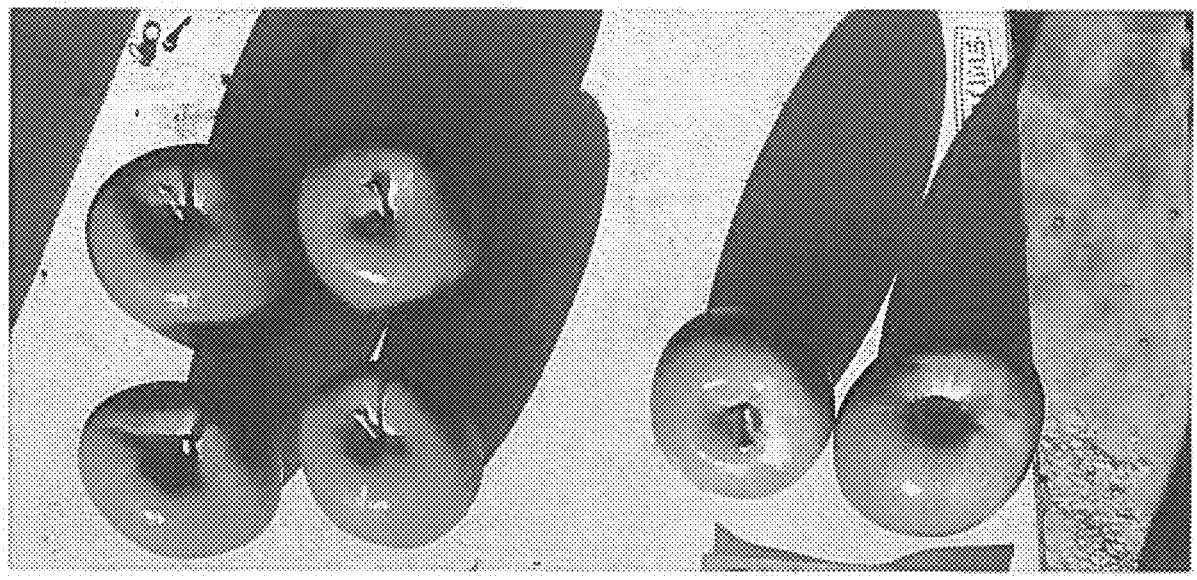
FIG. 4. Shows the difference in coloration between the mature fruit of 'MAIA1' (Right) and 'MAIA-MITCHELL' (Left) at the time of harvest.
Figure 5:
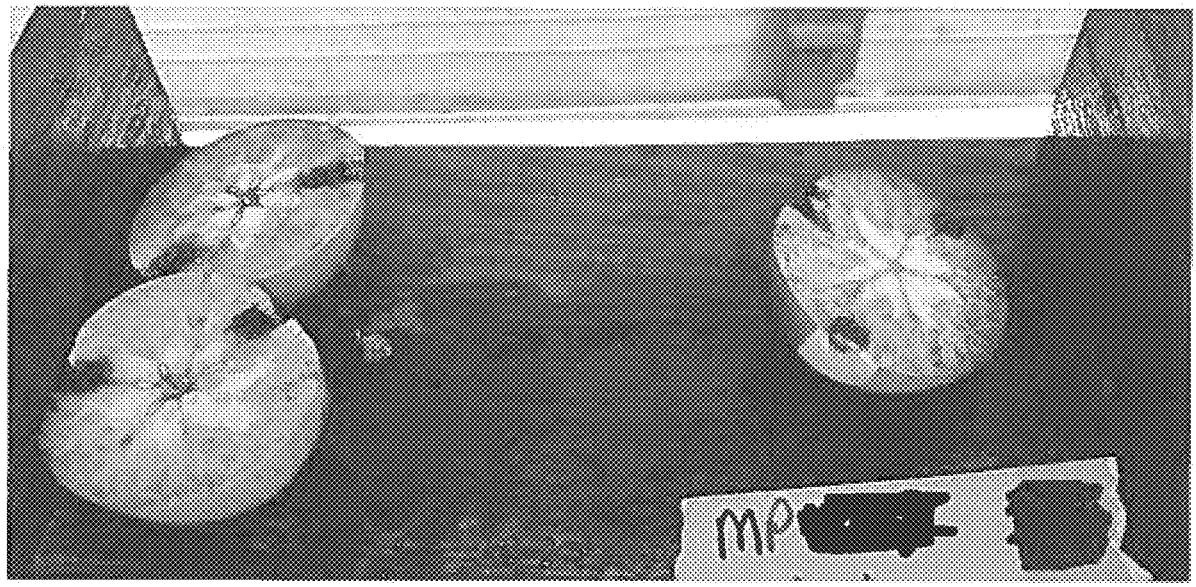
FIG. 5. Shows the iodine solution reactions for starch scoring of fruit of 'MAIA1' (Left) and 'MAIA-MITCHELL' (Right) harvested on the same day, illustrating comparable maturity timing.

Color references are made to The Royal Horticultural Society Colour Chart (R.H.S.) 2001 Edition.

Parentage: Limb mutation of 'MAIA1' (U.S. Plant Pat. No. 24,579). Locality of the original discovery and observations are Wolcott, New York and Sterling, New York.

Grafted tree on B9 rootstock (reference tree):

*Age*.—5 years.
*Vigor*.—Moderate.
*Form*.—Round, spreading with moderate density.
*Production*.—Very productive; 2.5 bushels/tree at 300 trees/acre=750 bushels/acre.
*Growth type*.—Non-spur with very weak dominance.
*Bearing*.—Annual.

Trunk:

*Bark color*.—Grey-Brown 199A.
*Lenticels*.—Oblong, 2.5×1.5 mm.
*Lenticel color*.—Grey Brown 199B.
*Lenticel density*.—6 lenticels/cm$^2$ on average.

Branches:

3 *year old*.—16-22 mm in diameter, branch angle 80-90°, Grey-Brown 199A.
2 *year old*.—14-18 mm in diameter, branch angle 80°90°, Grey-Brown 199A.
1 *year old*.—9-10 mm in diameter, branch angle 80°90°, Grey-Brown 199D.
*Average shoot internode length* (1 *year old branches*).—26 mm.
*Average number of lenticels per square cm*.—14.

Leaves:

*Size*.—Length 75 mm; width 55 mm.
*Texture*.—Leathery, crisp.
*Form*.—Ovate.
*Base*.—Roundly cuneate.
*Apex*.—Acute.
*Adaxial surface pubescence*.—None.
*Abaxial surface pubescence*.—Finely pubescent.
*Adaxial surface color*.—Yellow-Green 146B.
*Abaxial surface color*.—Yellow-Green 146D.
*Venation*.—Pinnate, 8-9 major veins; mainly alternate; Yellow-Green 149D.
*Margin*.—Serrate.
*Petiole length*.—30 mm.
*Petiole width*.—3 mm.
*Petiole abaxial color*.—Yellow-Green 145A to Greyed Purple 185C toward base and abscission layer on larger leaves.
*Petiole groove*.—Very shallow, depth 0.1 mm.
*Stipules*.—Present; 5 mm length; 1 mm width; Yellow Green 146D.
*Leaf glands*.—None observed.
*Leaf attitude*.—Upwards at a 30 degree angle.

Leaf buds:

*Length*.—1.5 mm.
*Width*.—1.5 mm.
*Color*.—Yellow-Green 145B with Greyed-Purple 185B overtones.
*Placement on branch*.—Alternate.
*Internode distance*.—25 mm.

Spurs: Present on 2 yr and older wood.

*Length*.—Varies from 10 to 350 mm.
*Proportion*.—350 mm: 1; 200-350 mm: 3; 100-200 mm: 3; 50-100 mm: 3; 10-50 mm: 3.
*Width*.—Short: 3.5 mm; Medium: 5 mm; Long: 7 mm.

Flowers at popcorn stage:

*Pedicel*.—Length 12-15 mm; diameter 2 mm.
*Pedicel color*.—Yellow-Green 148D.
*Bud*.—Length 7-9 mm; width 7 mm.
*Bud color*.—Red-Purple 63B, before flower petals expand and open; background of White 155C.

Flowers at full bloom:

*Bloom time*.—Blooms with 'Golden Delicious' and 'MAIA1'. Bloom time varies with temperature.
*Bloom period*.—Approximately 7 days but varies with temperature.
*Presentation*.—Showy.
*Fragrance*.—Aromatic.
*Fertility*.—Fertile.
*Corolla diameter*.—35-40 mm.
*Number of flowers per cluster*.—4-6 with 5 typical.

Petals:

*Arrangement*.—Bases overlapping; 5 petals per flower; each petal 15-18 mm length; 12-14 mm width.
*Color*.—Upper surface (inside) White 155C; lower surface (outside) White 155C with Red-Purple 70B overtones pronounced as flower begins to open and then fading as flower completely opens.
*Shape*.—Broadly ovate, abruptly cuneate at junction with receptacle.
*Veins*.—Non-distinct.
*Margins*.—Somewhat ruffled with occasional notching at the apex.
*Texture*.—Soft.
*Receptacle*.—Length 8 mm; width 6 mm; color Green 143D.
*Pedicel*.—Length 18-22 mm; width 2 mm; color Green 143D when pubescent; Reddish tones 58A as pubescence is lost as pedicel matures.
*Sepals*.—5/flower; wedge shaped; sharply pointed; length 6 mm; width 3 mm at widest point (attachment); color Greyed-Green 193B with Reddish Purple tip 58A.
*Stamens*.—18-22 in number.
*Anthers*.—Length 2 mm; width 1.5 mm; color Yellow 3D.
*Pollen*.—Present.
*Filaments*.—Length 5-12 mm, increasing in length as flower matures; width 0.5 mm; color Greyed-Green 193B.
*Pistil*.—Held lower than anthers in majority of blossoms.

*Ovary*.—Length 4 mm; width 3 mm; color Green 139B in cross section with Reddish Purple 60A layer under exterior pubescence.

*Style*.—Length 10 mm from fused base to Stigmas; width 1.5 mm at fused base; width 0.4 mm as separated styles; pubescent at point of separation from fused base; color Green 143A.

*Stigma*.—Width 1 mm; color Green 143A.

Pollination requirements: Requires cross-pollination from diploid varieties with overlapping bloom.

Fruit:

*Maturity when described*.—Freshly harvested.

*Date of picking*.—Oct. 26, 2022, in Wayne County NY.

*Size*.—Axial diameter 70-72 mm; Transverse diameter 80-85 mm.

*Fruit weight*.—average 238 g.

*Form*.—Roundish oblate regular.

*Cavity*.—Acuminate medium deep; russet extending out of cavity.

*Basin*.—shape, depth, width, medium depth, medium width, Symmetrical obtuse regular wavy.

*Calyx*.—Closed reflexed.

*Fruit aperture of eye*.—Closed.

Skin:

*Thickness*.—Medium.

*Tendency to crack*.—Little.

*Stripes*.—None.

*Lenticels*.—Round shape, 0.02-0.08 mm diameter, medium number per fruit.

*Color*.—Strong-red, 46A; overcolor pattern: only solid flush; bloom: light bloom coating.

*Ground color*.—Typically Greyed-red 180A, when fully colored but ground color can range in small areas from Brownish-orange 172C to Greyed-red 179B.

Flesh:

*Aroma*.—Sweet, aromatic.

*Color*.—Yellow-white 159B; void of pinkish or red coloration under skin or around core.

*Texture*.—Firm, crisp, and juicy.

*Flavor*.—Sweet.

Core: Medium size.

*Bundle area*.—250 $mm^2$.

*Bundle*.—Inconspicuous.

*Seed cells*.—Walls thin, tough.

*Locules*.—5 per fruit.

Seeds:

*Number perfect*.—10.

*Number in one cell*.—2.

*Length*.—9-10 mm.

*Breadth*.—5 mm.

*Color*.—Greyed-orange 165A.

Stem:

*Length*.—23-24 mm.

*Width*.—2.2 mm.

*Color*.—Greyed-yellow 162A.

Use: Fresh market, dessert.

Shipping quality: Apples maintain firmness and quality without bruising through shipping.

Keeping quality: Apples maintain fruit quality for 6 months under commercial refrigeration conditions.

Drought tolerance: Average for domestic apple.

Tree winter hardiness: Zones 6a to 8b (according to 2023 USDA Plant Hardiness Zone Map).

Disease resistance: No known resistance to pathogens.

I claim:

1. A new, distinct apple tree variety named 'MAIA-MITCHELL', as illustrated and described herein.

* * * * *